United States Patent [19]
Glover et al.

[11] Patent Number: 5,388,274
[45] Date of Patent: Feb. 14, 1995

[54] POWER BELT FOR HEAVY LIFTING

[75] Inventors: Dennis D. Glover; Cynthia M. Perez, both of Jackson, Mich.

[73] Assignee: DePuy Inc., Warsaw, Ind.

[21] Appl. No.: 103,337

[22] Filed: Aug. 6, 1993

[51] Int. Cl.$^6$ ............................................. A41F 3/02
[52] U.S. Cl. ................................... 2/338; 2/44; 2/311; 482/106; 482/139; 602/19; 602/20; 128/100.1; 128/96.1
[58] Field of Search ................. 2/2, 44, 311, 268, 336, 2/338; 602/19, 20; 482/106, 139; 450/155; 128/100.1, 101.1, 121.1, 96.1

[56] References Cited

U.S. PATENT DOCUMENTS

| | | | |
|---|---|---|---|
| 3,578,773 | 5/1971 | Schultz | 602/19 |
| 4,572,167 | 2/1986 | Brunswick | 2/44 |
| 4,782,535 | 11/1988 | Yewer, Jr. et al. | |
| 5,086,759 | 2/1992 | Buddingh | 602/19 |
| 5,122,111 | 6/1992 | Sebastian et al. | 602/19 |
| 5,147,261 | 9/1992 | Smith et al. | 2/338 |
| 5,188,586 | 2/1993 | Castel et al. | 602/19 |
| 5,195,948 | 3/1993 | Hill et al. | 602/19 |
| 5,205,815 | 4/1993 | Saunders | 602/19 |
| 5,257,419 | 11/1993 | Alexander | 602/19 |

OTHER PUBLICATIONS

"Valeo. The Revolutionary Approach to Effective Back Support", Valeo TM Advertising, one page, date unknown.
"Protect Your Bottom Line with Our Product Line", FLA Orthopedics Advertising, one page, date unknown.
"Strong and Comfortable", Valeo TM Advertising, one page, date unknown.
"Safety Products for Repetitive Motion Injuries", Safeguard Technologies Brochure, pp. 1–12, 1992.

*Primary Examiner*—Andrew M. Falik
*Assistant Examiner*—Gloria Hale
*Attorney, Agent, or Firm*—Barnes & Thornburg

[57] ABSTRACT

An improved orthopedic device for human wear comprising of a flexible belt encircling the human, with free ends thereof joined by a hook and loop fastener to position the belt on the wearer, and wherein the flexible belt is provided with a pad to be positioned against the lumbar and sacral regions of the wearer and with vertical stiffeners for the flexible belt. A static support is fixedly attached to the flexible belt and completely encircles the wearer. The static support is bi-level with one level encircling the wearer, extending around the flexible belt, and attached thereto adjacent the pad, and is provided with adjustable length belt buckle ends for cinching the one level about the user with varying degrees of tension. A second level is V-shaped and is attached to the elastic belt adjacent to the pad to dispense the support to the sacral regions when additional support is desired and the buckled clasp and first level tightened.

25 Claims, 2 Drawing Sheets

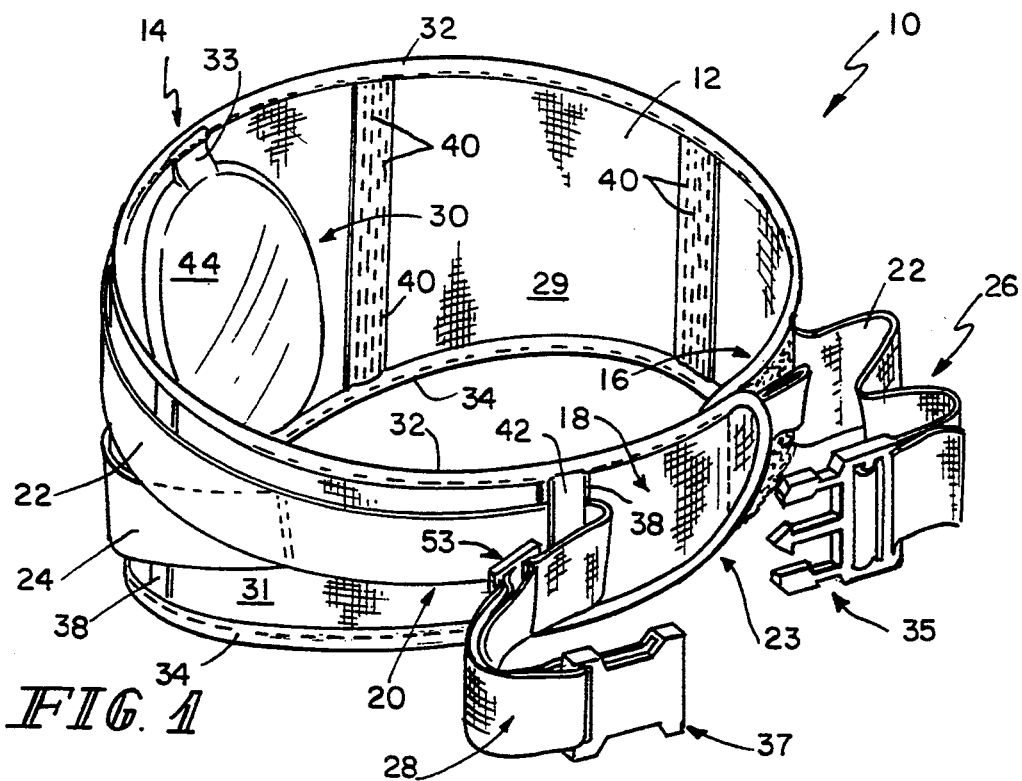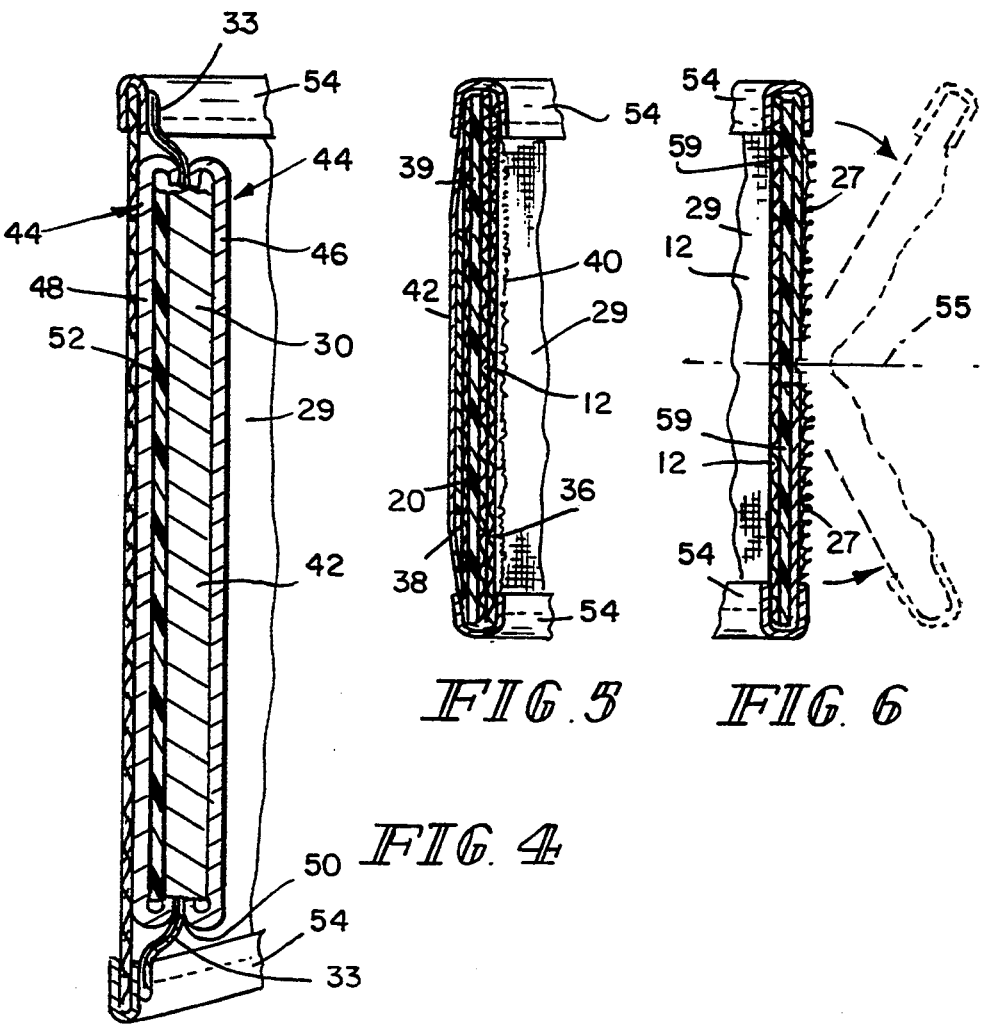

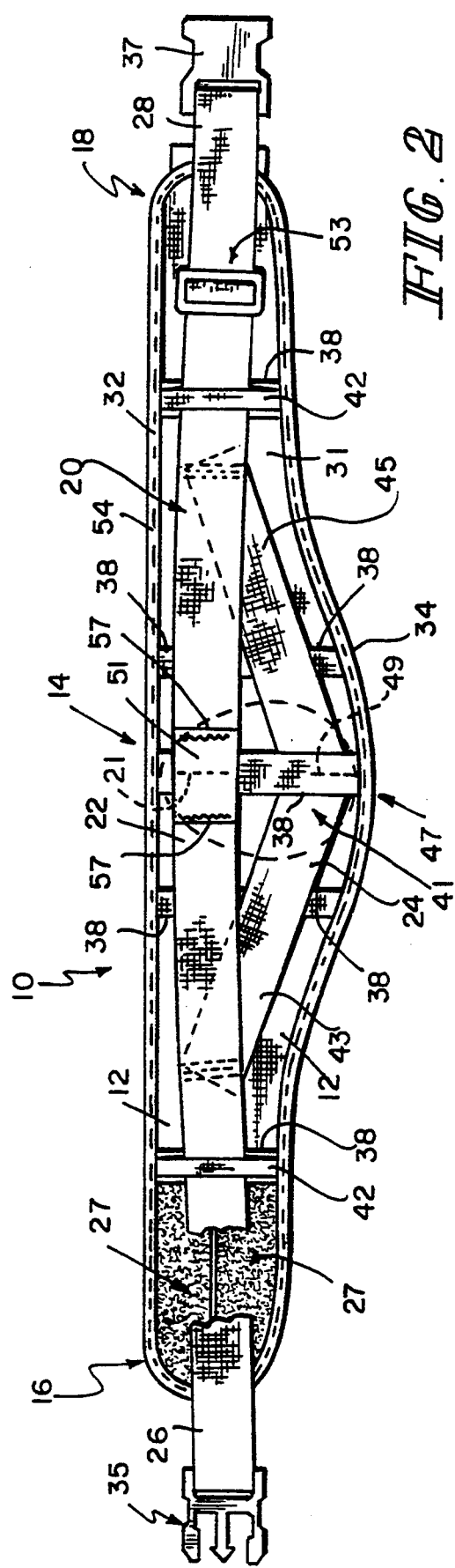
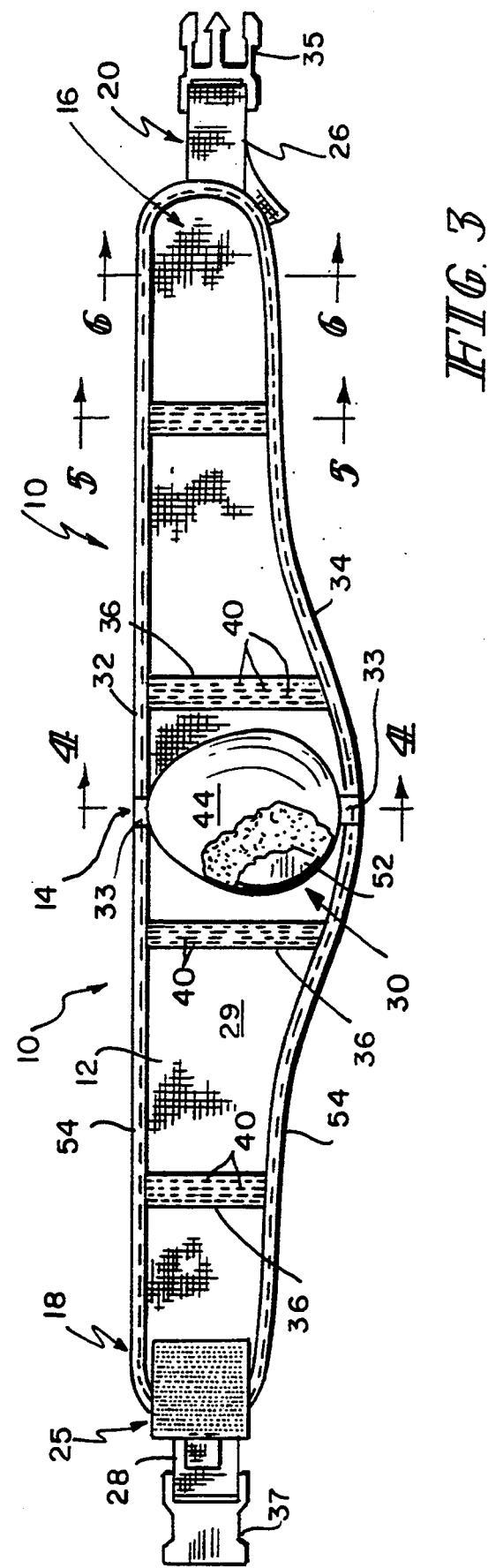

POWER BELT FOR HEAVY LIFTING

BACKGROUND AND SUMMARY OF THE INVENTION

The present invention relates to belts used for supporting the back and abdominal areas of a wearer, and particularly to belts that incorporate a form fitting pad to be positioned against the lumbar and sacral regions of the wearer. More particularly, the present invention relates to belts that combine a flexible band for holding the belt and pad in position and an adjustable static support structure for providing circumferential pressure to the back and abdominal areas of the wearer.

Back injury is the number one occupational health hazard in the U.S. While heavy lifting can be a cause of back injury, the most common cause is repetitive stress.

Repetitive stress can be experienced by almost any worker. For example, truck and cab drivers who sit much of the day are susceptible to stress induced back injury, as are doctors and nurses who spend much of their time bending over their work. Of course, construction, maintenance, and assembly line workers who repetitively bend over and lift loads as a part of their work are also at risk for back injury.

In the past, support belts have been used by workers to reduce the likelihood of back injury resulting from repetitive stress and lifting loads. In the trade, such support belts generally fall into two categories: rigid belts and flexible belts.

Rigid belts are used for support when lifting heavy weights. For example, weight lifters typically use rigid belts. A rigid belt provides good support, but pinches the pelvic wings (iliac crest) and the ribs when bending over or moving. Thus, rigid belts tend to be uncomfortable for most wearers.

Flexible belts are more comfortable than rigid belts, and are therefore more suitable for jobs requiring moving or bending over. Unfortunately, they provide less support than the rigid belts and are not suitable for work that requires any lifting. A support belt that combines the support of a rigid belt with the comfort of a flexible belt would be welcomed by workers and employers.

According to the present invention, a belt for supporting the lower back and abdominal regions of a wearer includes means for applying pressure against the lower back region of the wearer and elastic belt means coupled to the pressure applying means for holding the applying means in position. Static belt means is coupled to the elastic belt means for providing support to the pressure applying means.

The applying means comprises a back pad positioned against the lumbar and sacral regions of the wearer and held in position by the elastic belt means. The elastic belt means includes an elastic band that is attached to the back pad and configured to stretch along a longitudinal axis of the belt about the waist of the wearer. A plurality of vertical stays are attached to the elastic band and spaced longitudinally therealong and are configured to limit the amount of transverse stretching of the elastic band. A hook-and-loop closure is provided to couple the ends of the elastic band together to retain the back pad and the elastic band in position about the wearer's waist.

The static belt means includes a bi-level lockstrap having first and second static members. The first static member extends along a longitudinal axis of the elastic band to encircle the wearer's waist and is attached to the elastic band adjacent the back pad. A plurality of belt loops are attached to the elastic band to retain the first static member in a generally parallel relation with the longitudinal axis of the elastic band.

The second static member is attached to the first static member and extends downwardly therefrom to form a V-shaped projection. The V-shaped projection is attached to the elastic band adjacent the back pad and is configured to disperse the support to the sacral region of the wearer's spine. Thus, the static belt means works in combination with the back pad to provide support to the lumbar and sacral regions of the wearer.

The static belt means also includes a buckle for coupling the ends of the first static member together. The buckle includes means for adjusting the length of the first static member to fit the wearer and vary the amount of rigid support provided. Advantageously, the hook-and-loop closure on the elastic band holds the elastic band in position around the wearer's waist while the length of the first static member is independently adjusted.

By providing an elastic band coupled to a back pad and static means to rigidly support the elastic band and the back pad, the present invention provides the support of a rigid belt while eliminating the discomfort associated with rigid belts. Thus, the present invention combines the comfort of a flexible belt with the support of a rigid belt.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE INVENTION

FIG. 1 is a perspective view of a support belt constructed according to the-present invention having a back pad, an elastic band portion, first and second static members for providing rigid support, and a buckle for attaching the ends of the first static member together;

FIG. 2 is a plan view of the outside of the belt (as worn by a wearer) showing the first static member extending generally along a longitudinal axis of the belt, the second static member extending from the first static member to form a V-shaped projection, a loop portion of a hook-and-loop closure means, and a buckle attached to the ends of the first static member;

FIG. 3 is a plan view of the inside of the belt (as worn by a wearer) showing the back pad attached to the elastic band, vertical stays for limiting the amount of transverse stretching of the elastic band, and the hook portion of a hook-and-loop closure means;

FIG. 4 is a sectional view taken along line 4—4 of FIG. 3 showing the details of the back pad and its attachment to the elastic band;

FIG. 5 is a sectional view taken along line 5—5 of FIG. 3 showing the relative positioning of the stays, belt loops, and first static member; and FIG. 6 is a sectional view taken along line 6—6 of FIG. 3 showing the loop portion of the hoop-and-loop closure means bifurcated to allow the hook-and-loop closure to bend with the wearer.

DETAILED DESCRIPTION OF THE DRAWINGS

A support belt 10 constructed according to the present invention is shown in FIGS. 1–3. The support belt 10 includes an elastic band 12, a static belt 20, and a neoprene pad 30. The elastic band 12 extends longitudinally from a center portion 14 toward first and second ends, 16, 18, respectively. The static belt 20 is attached to the center portion 14 (as indicated at 21 in FIG. 2) of the elastic band 12 and includes first and second static members 22, 24, respectively. The static belt 20 extends longitudinally and adjacent the elastic band 12 between first and second ends 26, 28, respectively. The neoprene back pad 30 is attached to the center portion 14 of the elastic band 12 by a pair of straps 33.

The first and second ends 16, 18 of the elastic band 12 can be attached to each other by a conventional hook-and-loop closure 23 (FIG. 1). The closure 23 includes a hook portion 25 (FIG. 3) illustratively attached to the second end 18 and a loop portion 27 (FIG. 2) illustratively attached to the first end 16. The elastic band 12 is preferably made from Arloc elastic available at DePuy Inc. of Warsaw, Ind. 46581-0988, and includes inside and outside surfaces 29, 31, respectively, and top and bottom edges 32, 34, respectively.

A plurality of inside vertical stays 36 are attached to the inside surface 29 and extend between the top and bottom edges 32, 34. Matching outside vertical stays 38 are attached to the outside surface 31 of the elastic band 10 and longitudinally collocated with the inside vertical stays 36. The inside and outside vertical stays 36, 38 are preferably made from nylon webbing with high density polyethylene inserts 39. The vertical stays 36, 38 and the high density polyethylene inserts 39 cooperate with each other to maintain the shape of the support belt 10 while remaining flexible enough to bend with a wearer, thus making the support belt 10 more comfortable to wear than a rigid belt. Illustratively, a single high density polyethylene insert 39 is shown in FIG. 5 between the outside vertical stay 38 and the elastic band 12. Of course, additional inserts can be positioned between the inside vertical stays 36 and the elastic band 12 without exceeding the scope of the invention.

A plurality of rubber-band-like inserts 40 are stitched to the inside vertical stays 36 to provide a non-slip feature to help prevent the support belt 10 from migrating up or down on the wearer's clothing. A pair of elastic belt loops 42 are attached to outside vertical stays 38 at the top and bottom edges 32, 34. Illustratively, the belt loops 42 are attached to vertical stays 38 located adjacent the first and second ends 16, 18 of the elastic band 12. The belt loops 42 keep the static belt 20 generally aligned with the longitudinal axis of the support belt 10.

An additional piece of fabric 51 is stitched to the first static member 22 at 57. The additional piece of fabric 51 provides a suitable means for displaying a corporate logo.

As shown in FIG. 5, the inside and outside vertical stays 36, 38 are stitched to each other and to the rubber-band-like inserts 40 through the elastic band 12. However, the static belt 20 is free to move vertically in the space formed between the outside vertical stay 38 and the belt loop 42.

As best shown in FIG. 2, the static belt 20 includes first and second static members 22, 24, respectively. The first static member 22 is attached to the outside surface 31 of the elastic band 12 adjacent the upper end (relative to a wearer) of the back pad 30 (as indicated at 21 in FIG. 2). The first static member 22 extends generally along a longitudinal axis of the elastic band 12 and includes the first and second ends 26, 28. The first and second ends 26, 28 can be coupled together by an adjustable buckle having a blade portion 35 illustratively coupled to the first end 26 in a conventional fashion and a receiver portion 37 illustratively coupled in a conventional fashion to the second end 28. The adjustable buckle allows the wearer to adjust the length of the first end 26 of the static belt 20 to vary the amount of support provided by the support belt 10. An additional conventional adjustment buckle 53 is incorporated into the second end 28 of the static belt 20 to allow the wearer to adjust the length of the second end 28 of the static belt 20. A suitable buckle is the FASTEX SR-2 buckle produced by ITW NEXUS of Wood Dale, Ill. 60191.

The present invention achieves a major advantage by incorporating separate closure means for the elastic band 12 and the static belt 20. The hook-and-loop closure 23 holds the elastic band 12 in position on the wearer's waist independent of the static belt 20. The wearer can maintain the static belt 20 in a "normal support" configuration for long term support and comfort. If and when the job requires heaving lifting, the wearer can tighten the static belt 20 to increase the support. When the additional support is no longer needed, the static belt 20 can be loosened to the normal support configuration. Thus, the hook-and-loop closure 23 allows quick and easy adjustment of the static belt 20 without removing the entire belt 10 or changing the position of the pad 30 on the wearer.

The second static member 24 is attached to the first static member 22 and extends downwardly therefrom to form a V-shaped projection 41. The V-shaped projection 41 includes first and second straps 43, 45 which are attached to the first static member 22 and are stitched to each other to form the point 47 of the V-shaped projection 41. The point 47 is preferably stitched, or otherwise attached (as indicated in FIG. 2), to the center portion 14 of the elastic band 12 adjacent the lower end (relative to a wearer) of the back pad 30. A vertical stay 38 is attached to the elastic band 12 by stitching that passes through the point 47 and the first static member 22 so as to provide additional means for attaching the first and second static members 22, 24 to the elastic band 12.

Advantageously, by attaching the first and second static members 22, 24 to the upper and lower ends, respectively, of the back pad 30, the present invention provides a bi-level "static belting mechanism". The bi-level static belting mechanism assists in dispersing the support down to the sacral region of the spine, whereas other belts focus on the lumbar region of the spine.

Referring to FIG. 4, the back pad 30 is preferably made of a layered neoprene core 42 surrounded by a foam cover 44, wherein the layered neoprene performs a form fitting function for the back pad 30. The foam cover 44 includes front and back pieces 46, 48, respectively, stitched together at a circumferential seam 50. The straps 33 are attached to the foam cover 44 at the seam 50. Thus, the cover 44 and the straps 33 cooperate to attach the back pad 30 to the elastic band 12. A stiffener 52, preferably made of high density polyethylene, is positioned inside the foam cover 44 between the neoprene core 42 and the elastic band 12 to provide some firmness to the back pad 30. It will be appreciated that the core 42, cover 44, and stiffener 46 can be made of other materials without exceeding the scope of the invention.

As seen in FIG. 6, the loop portion 27 of the hook-and-loop closure 23 is attached to the elastic band 12 so as to enclose a sheet 59 of high density polyethylene. The loop portion 27 and the sheet 59 are longitudinally bifurcated along a split line 55. Advantageously, the split line 55 allows the loop portion 27 to fold approximately in half as the wearer bends over, thereby minimizing discomfort due to the pinching of the pelvic wings (iliac crest) and ribs associated with rigid belts while continuing to maintain support to the sacral and lumbar regions of the back. At the same time, the sheet 12 of high density polyethylene distributes the force of the static belt 20 when the belt is tightened.

Finally, a border strip 54 extends perimetrally around the elastic band 12. As shown in FIGS. 4-6, the border strip 54 is configured to cover the top and bottom edges 32, 34 of the elastic band 12 as well as the upper and lower ends of the vertical stays 36, 38, the belt loops 42, and the loop portion 27. Thus, the stitching that holds the border strip 54 to the elastic band 12 provides additional attachment means for the vertical stays 36, 38, the belt loops 42, and the loop portion 27. The straps 33 attaching the back pad 30 to the elastic band 12 are stitched to the outside of the border strip 54, as shown in FIG. 4.

Although the invention has been described in detail with reference to a certain preferred embodiment, variations and modifications exist within the scope and spirit of the invention as described and defined in the following claims.

We claim:

1. A belt for supporting the lower back and abdominal regions of a wearer, the belt comprising
   means for applying pressure against the lower back region of the wearer,
   elastic means coupled to the applying means for holding the applying means in position, the elastic means being stretchably positionable the waist area of the wearer, and
   static means for providing support to the pressure applying means, the static means being relatively inelastic and positionable about the waist area of the wearer to enclose the elastic means, the static means being bifurcated along a longitudinal axis of the elastic means to disperse the support to the sacral region of the wearer's spine.

2. The belt of claim 1, wherein the static means includes a lockstrap having a first static member extending generally along a longitudinal axis of the belt to encircle the wearer's waist, the first static member being fixed to the elastic means adjacent the applying means whereby longitudinal movement of the first static member relative to the elastic means is eliminated.

3. The belt of claim 2, wherein the dispersing means further includes a second static member attached to the first static member and extending downwardly from the first static member to form a V-shaped projection.

4. The belt of claim 3, wherein the second static member is fixed to the elastic means adjacent the applying means whereby longitudinal movement of the second static member relative to the elastic means is eliminated.

5. The belt of claim 1, wherein the elastic means includes an elastic band that is configured to stretch generally along a longitudinal axis of the belt and about the waist of the wearer.

6. The belt of claim 5, wherein the elastic means further includes vertical stay means for limiting the amount of transverse stretching of the elastic band.

7. The belt of claim 1, wherein the static means further includes a first end and a second end and means for coupling the first and second ends together, the coupling means including means for adjusting the length of the static means to vary the amount of support provided.

8. The belt of claim 7, wherein the elastic means includes means for closing the elastic band about the waist of the wearer to hold the pressure applying means in position while the length of the static means is adjusted to a selected tightness.

9. The belt of claim 1, further including first means for fastening and second means for fastening, the first means being attached to the elastic means to hold the elastic means in position on the wearer and the second means being attached to the static means, wherein the second means includes means for varying the amount of support provided.

10. The belt of claim 9, wherein the first means includes loop means for receiving hooks, the loop means being attached to a first end of the belt and the hooks being attached to a second end of the belt, the loop means being bifurcated along the longitudinal axis of the elastic means to facilitate bending along the axis as the wearer bends over.

11. The belt of claim 1, wherein the static means includes means for adjusting the static means to vary the amount of support provided by the static means to vary the pressure applied by the applying means.

12. The belt of claim 1, wherein the applying means includes a back pad having a resilient portion, a stiffener portion, a cover portion enclosing the resilient portion and the stiffener portion anti two straps attached to the cover portion, the tabs being coupled to the elastic means.

13. The belt of claim 12, further including means for fixing the back pad to the static means to eliminate movement of the back pad relative to the static means so that the back pad and the static means cooperate to maintain normal curvature of the weaxer's spine.

14. A belt for encircling and supporting the lower back and abdominal regions of a wearer, the belt comprising
   elastic belt means for encircling the waist area of the wearer, the elastic belt means having first and second ends to join in front of the wearer,
   a back pad having a resilient portion, a stiffener a cover portion enclosing the resilient portion and the stiffener portion, and two straps attached to the cover portion, the straps being coupled to the elastic belt means,
   first means for coupling the first and second ends of the elastic means together to hold the elastic means and back pad in position on the wearer,
   static belt means fixedly secured to the elastic belt means and encircling the wearer for providing support to the back pad and elastic means, the static belt means having first and second ends, and
   second means for coupling the first and second ends of the static belt means together to maintain the support to the elastic means and back pad, said second coupling means providing for tensioning and loosening of said static belt means without changing the tension of the elastic belt means.

15. The belt of claim 14, wherein the first means for coupling includes hook and loop fastening means having a hook portion and a loop portion, the loop portion being bifurcated about a longitudinal axis of the elastic means.

16. The belt of claim 15, wherein the second means for coupling includes a buckle having means for adjusting the length of the static belt means to vary the support provided by the static belt means.

17. The belt of claim 14, wherein the static belt means includes a bi-level lockstrap having a first static member extending generally along a longitudinal axis of the elastic means to encircle the wearer's waist and a second static member attached to the first static member and extending downwardly from the first static member to form a V-shaped projection.

18. The belt of claim 17, further comprising means for attaching the first and second static members to the elastic belt means to disperse the support to the sacral region of the wearer.

19. The belt of claim 14, further comprising belt loop means attached to the elastic belt means for maintaining the static, belt means in position relative to a longitudinal axis of the elastic means.

20. The belt of claim 14, wherein the elastic means includes a plurality of vertical stays, the vertical stays including means for limiting the amount of transverse stretching of the elastic band.

21. A belt for encircling and supporting the lower back and abdominal regions of a wearer, the belt comprising
a back pad,
an elastic waist band coupled to the back pad and configured to be positioned about the wearer's waist area and fastened in position on the wearer,
a lockstrap having first and second static members coupled to the elastic waist band, the first static member encircling the waist area of the wearer, and
means for adjusting the length of the lockstrap about the wearer thereby adjusting the tension on the lockstrap without adjusting the elastic waist band, the adjusting means cooperating with the back pad to apply pressure to the lumbar and sacral regions of the wearer to maintain normal curvature of the spine of the wearer.

22. The belt of claim 21, wherein the first static member extends along a longitudinal axis of the belt and the second static member is attached to the first static member and the elastic waist band, the second static member extending downwardly from the first static member to form a V-shaped projection.

23. The belt of claim 21, further comprising belt loop means attached to the elastic means for maintaining the lockstrap positioned relative to the elastic waist band.

24. The belt of claim 23, wherein the elastic waist band includes a plurality of vertical stays, the vertical stays including means for limiting the amount of transverse stretching of the elastic band.

25. A belt for supporting the lower back and abdominal regions of a wearer, the belt comprising
an elastic waist band configured to be positioned about the wearer's waist area,
a first static member extending along a longitudinal axis of the elastic waist band to encircle the waist of the wearer and provide support to the lower back and abdominal regions of the wearer,
a second static member coupled to the first static member and the elastic waist band so as to disperse the support to the sacral region of the wearer, and
means for adjusting the length of the first static member to increase or decrease the support provided by the first and second static members.

* * * * *